United States Patent
Von Hollen

(10) Patent No.: US 11,715,390 B2
(45) Date of Patent: Aug. 1, 2023

(54) TRAINING DEVICE FOR AN INHALER, AND AN INHALER

(71) Applicant: KONINKLIJKE PHILIPS N.V., Eindhoven (NL)

(72) Inventor: Dirk Ernest Von Hollen, Clark, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 1080 days.

(21) Appl. No.: 16/468,011

(22) PCT Filed: Dec. 18, 2017

(86) PCT No.: PCT/EP2017/083229
§ 371 (c)(1),
(2) Date: Jun. 10, 2019

(87) PCT Pub. No.: WO2018/109224
PCT Pub. Date: Jun. 21, 2018

(65) Prior Publication Data
US 2020/0013313 A1    Jan. 9, 2020

Related U.S. Application Data

(60) Provisional application No. 62/435,179, filed on Dec. 16, 2016.

(30) Foreign Application Priority Data

Jan. 10, 2017 (EP) ..................... 17150877

(51) Int. Cl.
*A61M 15/00*    (2006.01)
*G09B 23/28*    (2006.01)
*G09B 5/04*    (2006.01)

(52) U.S. Cl.
CPC ......... *G09B 23/28* (2013.01); *A61M 15/0001* (2014.02); *G09B 5/04* (2013.01);
(Continued)

(58) Field of Classification Search
CPC .... A61K 9/0043; A61K 31/335; A61K 31/58; A61K 47/02; A61K 47/183;
(Continued)

(56) References Cited

U.S. PATENT DOCUMENTS 5,167,506 A * 12/1992 Kilis ..................... G09B 23/28
128/200.14
5,363,842 A    11/1994 Mishelevich et al.
(Continued)

FOREIGN PATENT DOCUMENTS

JP    2013544156 A    12/2013
WO    WO-9217231 A1 *  10/1992   .......... A61M 15/008

OTHER PUBLICATIONS http://vitalograph.com/downloads/92/aim-leaflet.
(Continued)

*Primary Examiner* — Annette Dixon
(74) *Attorney, Agent, or Firm* — Daniel H. Brean; Andrew M. Gabriel

(57) ABSTRACT

According to an aspect, there is provided a training device for use in an inhaler, the training device comprising a body that is configured to be received at a first position in a housing of an inhaler, wherein the body comprises an interface arranged to connect to a canister interface in the housing of the inhaler; an electrical circuit configured to perform one or more functions; and a circuit triggering mechanism that comprises a switch for enabling the electrical circuit to perform the one or more functions when the switch is closed, wherein the circuit triggering mechanism is configured such that the switch is closed when the body is (Continued)

pressed from the first position towards the canister interface and into a second position in the housing of the inhaler.

20 Claims, 4 Drawing Sheets

(52) U.S. Cl.
CPC ............... *A61M 2205/332* (2013.01); *A61M 2205/3327* (2013.01); *A61M 2205/3334* (2013.01); *A61M 2205/3553* (2013.01); *A61M 2205/581* (2013.01); *A61M 2205/587* (2013.01)

(58) Field of Classification Search
CPC ...... A61K 47/186; A61K 47/24; A61K 47/26; A61K 47/38; A61K 9/10; A61K 47/36; A61M 11/007; A61M 15/0065; A61M 15/08; A61M 31/00; A61M 2210/0618; A61M 2202/0468; A61M 2205/0238; A61M 11/00; A61M 11/002; A61M 11/003; A61M 11/005; A61M 11/006; A61M 11/04; A61M 11/06; A61M 11/08; A61M 15/00; A61M 15/0005; A61M 15/0013; A61M 15/0016; A61M 15/0018; A61M 15/0021; A61M 15/0023; A61M 15/0025; A61M 15/0026; A61M 15/0028; A61M 15/003; A61M 15/0043; A61M 15/0045; A61M 15/0051; A61M 15/0066; A61M 15/0068; A61M 15/0071; A61M 15/0076; A61M 15/008; A61M 15/0081; A61M 15/0083; A61M 15/0085; A61M 15/0086; A61M 15/009; A61M 15/0091; A61M 15/0095; A61M 15/0096; A61M 15/025; A61M 16/0003; A61M 16/0051; A61M 16/0063; A61M 16/021; A61M 16/06; A61M 16/0616; A61M 16/0858; A61M 16/202; A61M 2005/31588; A61M 2016/0015; A61M 2016/0021; A61M 2016/0024; A61M 2016/0027; A61M 2016/003; A61M 2016/0036; A61M 2016/0039; A61M 2016/0042; A61M 2202/064; A61M 2205/0266; A61M 2205/0288; A61M 2205/071; A61M 2205/123; A61M 2205/128; A61M 2205/13; A61M 2205/14; A61M 2205/18; A61M 2205/183; A61M 2205/276; A61M 2205/33; A61M 2205/3306; A61M 2205/332; A61M 2205/3327; A61M 2205/3331; A61M 2205/3334; A61M 2205/3368; A61M 2205/3375; A61M 2205/3393; A61M 2205/35; A61M 2205/3546; A61M 2205/3553; A61M 2205/3561; A61M 2205/3569; A61M 2205/3576; A61M 2205/3584; A61M 2205/3592; A61M 2205/3653; A61M 2205/43; A61M 2205/44; A61M 2205/50; A61M 2205/502; A61M 2205/505; A61M 2205/52; A61M 2205/58; A61M 2205/581; A61M 2205/582; A61M 2205/583; A61M 2205/584; A61M 2205/587; A61M 2205/60; A61M 2205/6018; A61M 2205/6027; A61M 2205/6036; A61M 2205/6045; A61M 2205/6054; A61M 2205/70; A61M 2205/8206; A61M 2205/8212; A61M 2205/825; A61M 2209/02; A61M 2209/084; A61M 2209/086; A61M 2230/40; A61M 2230/50; A61M 2230/63; A61M 5/20; A61M 5/31546; A61P 37/08; A61P 11/02; A61P 27/14; B05B 15/30; B05B 11/0037; A61B 2560/242; A61B 2560/0276; A61B 2560/028; A61B 2560/0462; A61B 2562/0247; A61B 5/0022; A61B 5/087; A61B 5/0871; A61B 5/0876; A61B 5/091; A61B 5/097; A61B 5/1112; A61B 5/4833; A61B 5/4839; A61B 5/4848; A61B 5/486; A61B 5/742; A61B 5/746; A61B 8/0875; A61J 2200/30; A61J 2200/70; A61J 7/0418; A61J 7/0436; A61J 7/0481; A61N 7/00; A63B 2071/0625; A63B 2071/0694; A63B 21/0087; A63B 23/18; A63B 23/185; B01F 23/2132; B01F 35/71; B01F 35/7179; F16H 35/00; G01F 1/363; G01F 1/40; G01F 1/44; G01F 1/50; G01F 1/66; G01F 1/666; G01F 13/006; G01F 15/002; G01F 25/10; G01F 7/005; G06Q 50/22; G08B 21/24; G09B 23/28; G16H 10/20; G16H 20/10; G16H 20/13; G16H 40/67; G16H 70/40; H04W 4/023; H04W 4/80; Y02A 90/10

See application file for complete search history.

(56) References Cited

U.S. PATENT DOCUMENTS

| | | | |
|---|---|---|---|
| 5,404,871 A | 4/1995 | Goodman et al. | |
| 5,809,997 A | 9/1998 | Wolf | |
| 6,029,659 A | 2/2000 | O'Connor | |
| 6,435,177 B1 | 8/2002 | Engelbreth et al. | |
| 6,651,651 B1 | 11/2003 | Bonney et al. | |
| 6,752,145 B1 | 6/2004 | Bonney et al. | |
| 7,151,456 B2 * | 12/2006 | Godfrey | A61M 15/009 128/200.14 |
| 7,191,777 B2 * | 3/2007 | Brand | A61M 15/0065 128/200.23 |
| 7,819,116 B2 * | 10/2010 | Brand | A61M 15/0068 128/200.23 |
| 7,832,394 B2 * | 11/2010 | Schechter | A61M 15/009 128/203.14 |
| 7,896,002 B2 | 3/2011 | Watanabe | |
| 8,091,545 B2 * | 1/2012 | Schechter | A61M 15/009 222/64 |
| 8,397,714 B2 | 3/2013 | Farr et al. | |
| 2002/0090601 A1 * | 7/2002 | Strupat | A61M 15/0005 434/363 |
| 2002/0189612 A1 * | 12/2002 | Rand | A61M 15/0068 128/200.23 |
| 2005/0022806 A1 | 2/2005 | Beaumont et al. | |
| 2005/0028815 A1 | 2/2005 | Deaton et al. | |
| 2006/0254581 A1 * | 11/2006 | Genova | A61M 15/009 128/200.23 |
| 2008/0023001 A1 | 1/2008 | Watanabe | |
| 2011/0226242 A1 | 9/2011 | Von Hollen et al. | |
| 2013/0008436 A1 | 1/2013 | Von Hollen et al. | |
| 2013/0151162 A1 | 6/2013 | Harris et al. | |
| 2015/0061867 A1 | 3/2015 | Engelhard et al. | |
| 2015/0174349 A1 | 6/2015 | Tunnell et al. | |
| 2016/0049096 A1 | 2/2016 | Clarke et al. | |
| 2016/0144142 A1 | 5/2016 | Baker et al. | |
| 2016/0228657 A1 | 8/2016 | Sutherland | |
| 2016/0325058 A1 | 11/2016 | Samson et al. | |

OTHER PUBLICATIONS www.clement-clarke.com/ProductInfo/InhalerTechniqueTraining/NEWTrainhaler.aspx.

(56) References Cited

OTHER PUBLICATIONS

International Search Report—PCT/EP2017/083229 filed Dec. 18, 2017.

* cited by examiner

TRAINING DEVICE FOR AN INHALER, AND AN INHALER

CROSS-REFERENCE TO PRIOR APPLICATIONS

This application claims the priority benefit under 35 U.S.C. § 371 of International Patent Application No. PCT/EP2017/083229, filed on Dec. 18, 2017, which claims the priority benefit of U.S. Provisional Patent Application No. 62/435,179, filed Dec. 16, 2016, and European Patent Application No. 17150877.3, filed on Jan. 10, 2017, the contents of which are herein incorporated by reference.

FIELD OF THE INVENTION

The invention relates to a training device for an inhaler and an inhaler comprising such a training device.

BACKGROUND OF THE INVENTION

It has been found that compliance with respiratory medication therapy is suboptimal in terms of medication use, scheduling and correctness of inhalation technique for pressurised metered dose inhalers (pMDIs). Critical errors in inhaler use are strongly associated with poorer disease control than in patients that have the correct technique. It has been found that a majority of patients have difficulty in using a pMDI properly, and studies have shown that only 30% of patients use them correctly, and that number declines as early as two months after starting treatment.

Respiratory treatments place a significant burden on the lives of patients with respiratory diseases. Devices are difficult to use correctly, and incorrect use results in no or low delivery of medication, and can result in a worsening of patients' conditions. Patients with asthma or COPD (chronic obstructive pulmonary disease) may also require the use of multiple medications to manage their disease. Medication adherence in patients with chronic diseases is typically 50% of that prescribed. Having to take multiple medications reduces this further.

Pharmaceutical companies sometimes provide placebo training canisters to physicians, however, these are typically filled with propellant and do not contain an active drug. Supply of these placebo canisters is limited, and, when commercially available, the propellant filled canister is relatively expensive, and each canister is for use by a single patient.

Electronic training systems are also commercially available that provide active feedback that can be monitored by a medical professional, but these systems also require the use of a propellant driven inhaler. An example of such a training system is the Vitalograph AIM.

A significant disadvantage with these propellant driven inhalers is that the patient needs to repeatedly inhale the propellant, e.g. chlorofluorocarbon or hydroflouralkane chemicals, which exit the canister in order to practice proper administration (inhalation) technique. Both chemicals are known to be harmful to the environment.

SUMMARY OF THE INVENTION

Therefore there is a need for an improved training device for an inhaler, such as a pressurised metered dose inhaler (pMDI), that addresses one or more of the above disadvantages.

According to a first aspect, there is provided a training device for use in an inhaler, the training device comprising a body that is configured to be received at a first position in a housing of an inhaler, wherein the body comprises an interface arranged to connect to a canister interface in the housing of the inhaler; an electrical circuit configured to perform one or more functions; and a circuit triggering mechanism that comprises a switch for enabling the electrical circuit to perform the one or more functions when the switch is closed, wherein the circuit triggering mechanism is configured such that the switch is closed when the body is pressed from the first position towards the canister interface and into a second position in the housing of the inhaler.

In some embodiments, the circuit triggering mechanism comprises a resilient component configured to provide a force that resists the pressing of the body into the housing of the inhaler. In these embodiments, the resilient component is configured to return the body to the first position in the inhaler when the body is not pressed. In some embodiments, the resilient component comprises a spring or a spring-like component.

In some embodiments, the distance between the first position and the second position corresponds to the distance moved by a medication canister received in the housing of the inhaler when medication is to be dispensed.

In some embodiments, the electrical circuit comprises a sound producing unit, and the one or more functions comprises the sound producing unit producing a sound. The sound can be an audible sound and/or a sound that has a frequency in the ultrasonic range. The sound producing unit may be configured to produce a sound corresponding to the sound of medication being dispensed from an inhaler.

In some embodiments, the electrical circuit comprises a light producing unit, and the one or more functions comprises the light producing unit producing light.

In some embodiments, the electrical circuit comprises one or more sensors, and the one or more functions comprises operating the sensors to measure one or more parameters relating to use of the training device by a user. The one or more parameters can comprise any one or more of movements of the training device, movements of the training device relative to the housing of the inhaler, orientation of the training device, a force exerted on the training device, the air flow through the housing of the inhaler and whether a user is holding their breath after the body is moved to the second position. In these embodiments, the electrical circuit can also comprise a feedback device for providing feedback to the user on the use of the training device based on the measured one or more parameters. The feedback device may be configured to provide feedback on a sequence of events performed by the user in using the training device. In some embodiments, the electrical circuit further comprises a transmitter for transmitting the measurements of the one or more parameters to a remote electronic device.

In some embodiments, the electrical circuit is also configured to monitor movements of the training device before the body is pressed into the second position in the housing of the inhaler.

In some embodiments, the electrical circuit is also configured to monitor air flow through the housing of the inhaler before the body is pressed into the second position in the housing of the inhaler.

According to a second aspect, there is provided an inhaler that comprises a housing having a canister interface; and a training device according to any of the embodiments described above.

According to a third aspect, there is provided a method of training a user to operate an inhaler, the method comprising providing a training device that comprises a body that is configured to be received at a first position in a housing of an inhaler, wherein the body comprises an interface arranged to connect to a canister interface in the housing of the inhaler, an electrical circuit configured to perform one or more functions, and a circuit triggering mechanism that comprises a switch for enabling the electrical circuit to perform the one or more functions when the switch is closed, and wherein the circuit triggering mechanism is configured such that the switch is closed when the body is pressed from the first position towards the canister interface and into a second position in the housing of the inhaler; and enabling the electrical circuit to perform the one or more functions when the body is pressed into the second position in the inhaler.

In some embodiments, the electrical circuit comprises a sound producing unit, and the one or more functions comprises the sound producing unit producing a sound. In these embodiments, the method can further comprise producing a sound using the sound producing unit. The step of producing a sound may comprise producing an audible sound, such as a sound corresponding to the sound of medication being dispensed from an inhaler and/or a sound that has a frequency in the ultrasonic range.

In some embodiments, the electrical circuit comprises a light producing unit, and the one or more functions comprises the light producing unit producing light. In these embodiments, the method can further comprise the step of producing light using the light producing unit.

In some embodiments, the electrical circuit comprises one or more sensors, and the method further comprises the step of operating the sensors to measure one or more parameters relating to use of the training device by a user. The one or more parameters may comprise any one or more of movements of the training device, movements of the training device relative to the housing of the inhaler, orientation of the training device, a force exerted on the training device, the air flow through the housing of the inhaler and whether a user is holding their breath after the body is moved to the second position.

In some embodiments, the electrical circuit further comprises a feedback device, and the method can further comprise the step of providing feedback to the user using the feedback device on the use of the training device based on the measured one or more parameters. In some embodiments, the method further comprises the step of providing feedback using the feedback device on a sequence of events performed by the user in using the training device.

In some embodiments, the electrical circuit further comprises a transmitter, and the method further comprises the step of transmitting the measurements of the one or more parameters to a remote electronic device.

In some embodiments, the method further comprises the step of using the electrical circuit to monitor movements of the training device before the body is pressed into the second position in the housing of the inhaler.

In some embodiments, the method further comprises the step of using the electrical circuit to monitor air flow through the housing of the inhaler before the body is pressed into the second position in the housing of the inhaler.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

An inhaler typically comprises a housing having a mouthpiece arranged to interface with a user's mouth, with the housing also being arranged to receive a canister comprising medication and propellant to force the medication towards the user's mouth upon actuation of the canister. Prior to use, a canister usually has to be shaken to mix the medication and propellant. The user then has to coordinate their inhalation with actuation of the canister and dispensing of the drug. As a result, proper use of inhalers is not entirely straightforward and requires experience in coordination on the part of the user. Improper use may result in too little medication being administered to a user.

The invention provides a training device for an inhaler than can be used to train a user of the inhaler in the correct technique for successfully administering a medicine or respiratory therapy. The training device can be used by a patient to train themselves to correctly use the inhaler, and/or the training device can be used by someone other than a patient to learn how to correctly use the inhaler on someone else (for example a care provider using an inhaler on a patient).

Although the invention is primarily described with reference to a metered dose inhaler (MDI) or pressurised MDI (pMDI), it will be appreciated that it can be used with other types of inhalers where a user has to press a component of the inhaler to trigger the release of a medication, such as dry powder inhalers, liquid spray inhalers or soft mist inhalers, for example.

Figure 1:
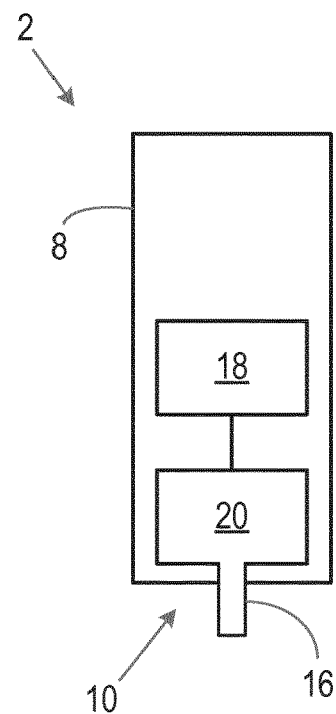
FIG. 1 is a block diagram of a training device according to an embodiment.
Figure 2:
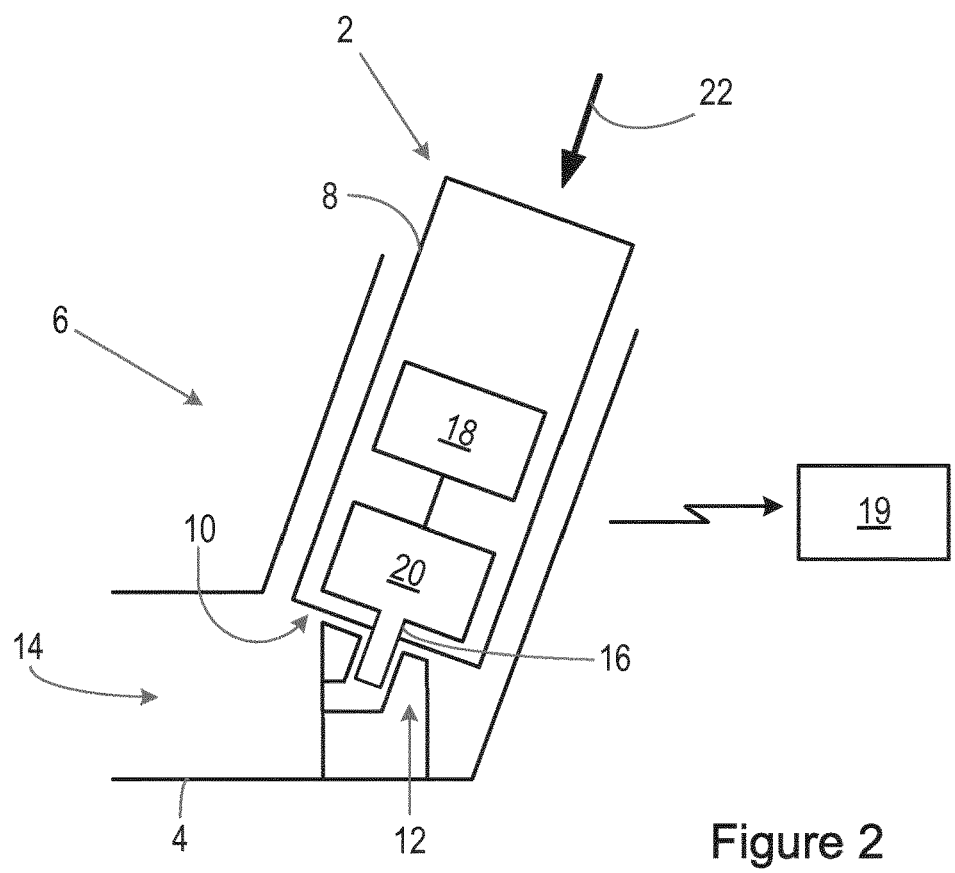
FIG. 2 is a block diagram of a training device according to an embodiment connected to a housing of an inhaler.

FIG. 1 is a block diagram of a training device 2 according to an embodiment of the invention. FIG. 2 is a block diagram of the training device 2 of FIG. 1 installed in a housing 4 of an inhaler 6.

The training device 2 is for use in an inhaler 6 in place of or instead of a medication canister, and the training device 2 comprises a body 8 that is configured to be received in a housing 4 of an inhaler 6. Preferably the training device 2 is for use in a conventional inhaler housing, i.e. a housing that is configured to receive a canister that contains medication, and thus the body 8 comprises an interface 10 that is arranged to connect to a canister interface 12 in the housing 4 of the inhaler 6. The interface 10 is preferably arranged or configured to enable the training device 2 to be removed from the housing 4, for example when a training exercise or training session has been completed. The training device 2 also preferably has a shape that is the same or similar to a conventional medication canister, and for example the body 8 can be generally cylindrical like a conventional canister. Thus the body 8, and training device 2 as a whole, can be canister-shaped. It will be appreciated that, due to the overall shape of the housing 4, the housing 4 is sometimes referred to as a 'boot'. The housing 4 also comprises a mouthpiece 14, or other type of interface through which a patient can inhale when the inhaler 6 is being used. When inserted into a housing 4 and no pressure or force is applied to the training device 2 by a user, the training device 2 will be in a first position in the inhaler 6, also referred to as a non-actuated position.

A medication canister that can conventionally be used in an inhaler 4 can comprise a stem or similar structure that can be received in a part 12 of the housing 4 (e.g. a canister interface 12) that enables the medication to be expelled from the canister upon actuation and inhaled by a patient that is inhaling through the mouthpiece 14. Thus, in some embodiments the interface 10 of the training device 2 can comprise a stem 16 that can also be received in the part of the housing 4 of the inhaler 6. It will be appreciated that, similar to a medication canister, the training device 2 is shaped or dimensioned so that the training device 2 fits inside the housing 4 and allows air to be drawn through the inhaler 6 when the patient inhales through the mouthpiece 14. Thus, for example, the training device 2 can have the same or substantially the same dimensions as a conventional medication canister that is to be used in the inhaler housing 4.

The training device 2 also comprises an electrical circuit 18 that is configured to perform one or more functions. In particular the one or more functions relate to training the user to use the inhaler 6 correctly or monitoring the use of the inhaler 6 by the user. For example, the one or more functions can comprise any of providing an output to the user indicating whether the inhaler 6 has been used correctly (for example a sound or light), measuring one or more aspects of the use of the inhaler 6, providing feedback to the user on the use of the inhaler 6, and providing information to a remote electronic device 19. Exemplary functions and components of the electrical circuit 18 are described in more detail below.

The remote electronic device 19, which is optional, can be used to provide feedback on the operation or use of the training device 2 to the user of the training device 2 or other interested party (for example a physician or other care provider of the user/patient). The remote electronic device 19 can comprise any suitable electronic device, such as a computer, desktop computer, laptop computer, tablet computer, server, smart phone, personal digital assistant, etc. In this case the remote electronic device 19 can operate or execute any suitable program for obtaining and presenting the feedback. It will be appreciated that the electronic device 19 can be remote in the sense that it is not directly connected the training device 2 or inhaler 6.

To selectively enable the electrical circuit 18, the training device 2 also comprises a circuit triggering mechanism 20 that comprises a switch for enabling the electrical circuit 18 to perform the one or more functions when the switch is closed. In particular, the circuit triggering mechanism 20 is configured such that when the body 8 (or rather the training device 2 as a whole) is pressed towards the canister interface 12 of the inhaler 6 (e.g. by a user) and into the housing 4 of the inhaler 6 (i.e. in a direction indicated by arrow 22), the switch is closed once the body 8 has moved a predetermined distance into the inhaler 6 (i.e. to the second position). Thus the electrical circuit 18 is enabled to perform the one or more functions when the body 8 is moved into the second position. It will be appreciated that enabling the electrical circuit 18 can comprise enabling the electrical circuit 18 to be powered (e.g. by connecting the electrical circuit 18 to a power supply), or enabling an already-powered electrical circuit 18 to perform the one or more functions.

In some embodiments, the circuit triggering mechanism 20 comprises a resilient component that is configured to provide a force that resists the pressing of the body 8 into the housing 4 of the inhaler 6 by a user. In some embodiments, the resilient component can require a force of between 15 and 25 Newton, for example around 17.7 Newton, in order to be pressed. Preferably, the resilient component provides a force that is equivalent or substantially equivalent to the force required to actuate a conventional medication canister. In this way, the circuit triggering mechanism 20 will provide the user with a similar experience to the actuation of a conventional medication canister. The resilient component can comprise a spring or a spring-like component. In some embodiments, the resilient component can be configured to return the body 8 to the first position in the inhaler 6 when the user is not pressing the body 8. Again, this provides the user with a similar experience to using a conventional medication canister, since the actuation mechanism for those canisters return the canister to the initial position when the user stops pressing the canister.

Preferably, the circuit triggering mechanism 20 is configured such that the distance that the body 8 is to be moved by a user in order to enable the electrical circuit 18 (i.e. the predetermined distance from the first position to the second position) is the same or similar to the distance moved by a conventional medication canister when actuated to dispense medication. For example, the circuit triggering mechanism 20 can allow for a movement of between 0.25 centimetres (cm) to 0.64 cm.

Figure 3:
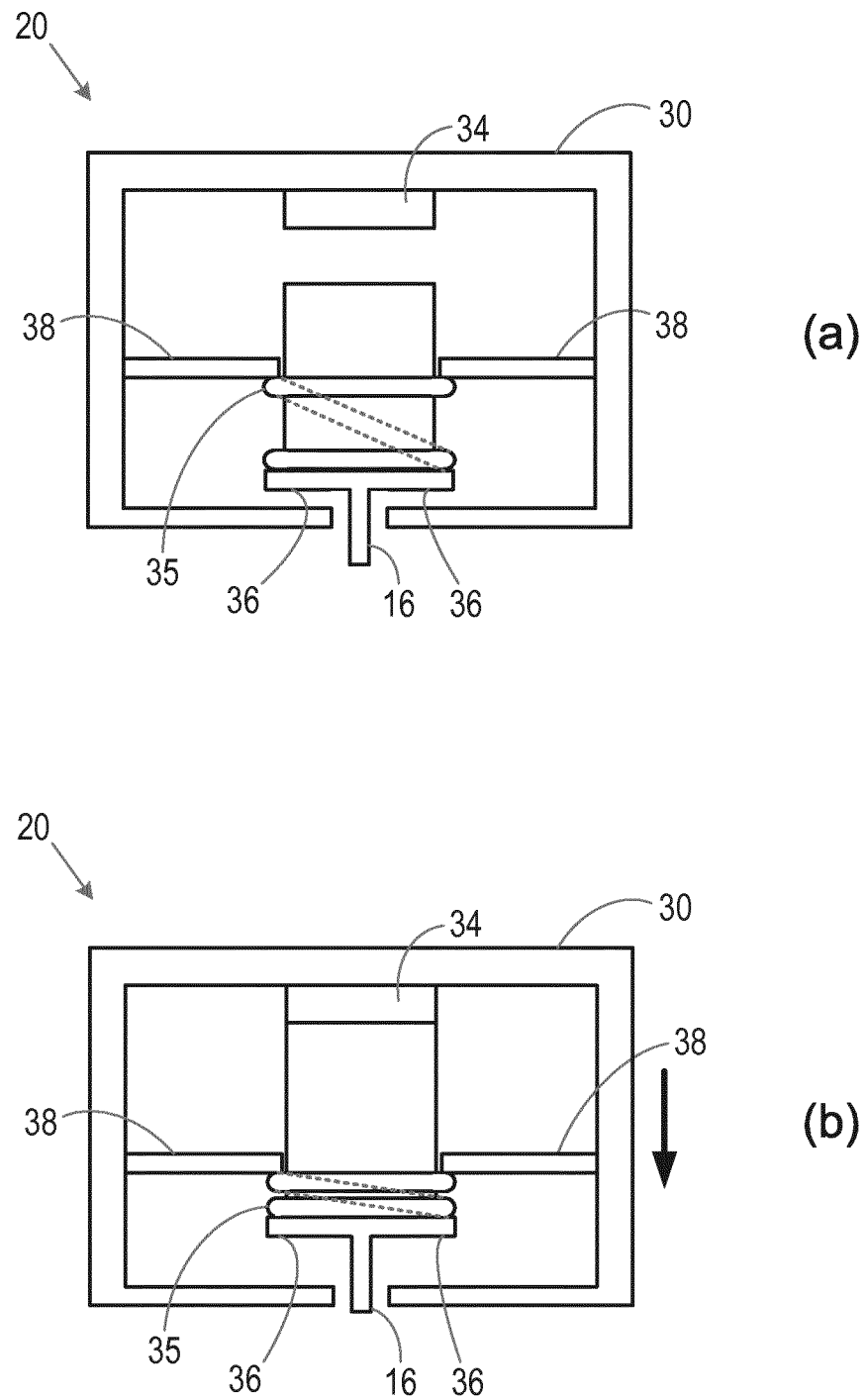
FIG. 3(a) is a diagram illustrating a circuit triggering mechanism according to an embodiment in an initial position and FIG. 3(b) is a diagram illustrating the circuit triggering mechanism in an actuated position.

FIG. 3 shows a circuit triggering mechanism 20 according to an exemplary embodiment. The circuit triggering mechanism 20 comprises a stem or plunger 16 that provides the interface 10 for enabling the training device 2 to be connected to the canister interface 12 in a housing 4 of an inhaler 6. The stem (plunger) 16 extends inside a housing 30 of the circuit triggering mechanism 20, with an upper portion 32 of the stem 16 that is to be used to activate a switch 34 when the body 8 is pressed into the housing 4. The stem 16 is moveable within the housing 30 from a first, initial, position, as shown in FIG. 3(a), to a second, actuated, position, in which the electrical circuit 18 is enabled, as shown in FIG. 3(b). The upper portion 16 closes the switch 34, and this enables the electrical circuit 18. As noted above, this enabling can comprise enabling the electrical circuit 18 to be powered (e.g. by connecting the electrical circuit 18 to a power supply), or enabling an already-powered electrical circuit 18 to perform the one or more functions. A resilient component 35 in the form of a spring is provided in the circuit triggering mechanism 20 in order to provide a force that resists the pressing of the body 8 into the inhaler 6 (and in preferred embodiments replicates the force required for a user to actuate a conventional medication canister). The spring 35 acts, at one end of the spring 35, on a shoulder 36 of the stem 16, and, at the other end of the spring 35, on a shoulder 38 of the housing 30 of the circuit triggering mechanism. Thus, when the body 8 is pressed into the inhaler 6, the stem 16 is pressed into the housing 30 of the circuit triggering mechanism 20, thereby compressing the spring 35 between the shoulders 36, 38, until the upper portion 32 of the stem 16 contacts the switch 34 and causes the enabling of the electrical circuit 18. In preferred embodiments, the distance that the stem 16 can move between the first position and the second position is the same or similar to the distance moved by a conventional medication canister during actuation. In some embodiments, the circuit triggering mechanism 20 can be configured such that the body 8 comes to a hard stop when moved to the second position, which is similar to the movement of a conventional medication canister in an inhaler 6.

As noted above, FIG. 3 shows an exemplary embodiment of the circuit triggering mechanism 20, and those skilled in the art will appreciate that other configurations of the circuit triggering mechanism 20 are possible that provide the functions described above.

Figure 4:
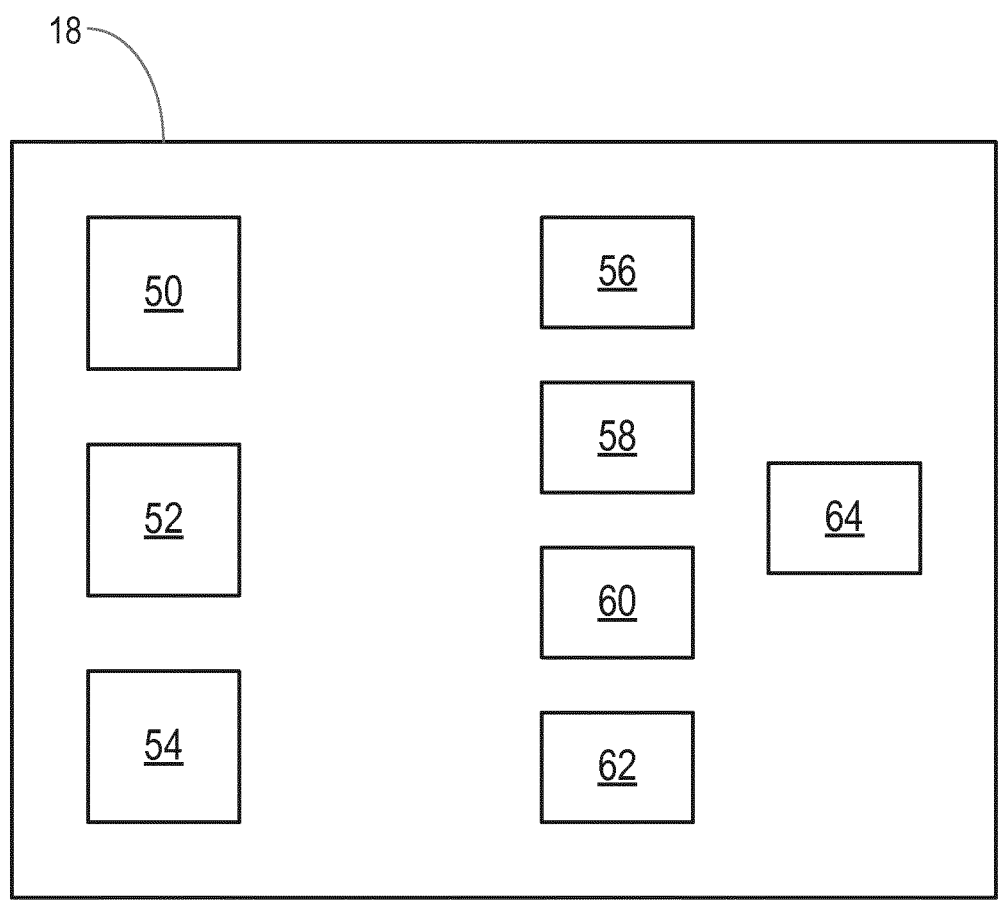
FIG. 4 is a block diagram of an exemplary electrical circuit.

FIG. 4 shows the components of an exemplary electrical circuit 18. In some embodiments, the electrical circuit 18 comprises a sound producing unit 50, for example a speaker, and the function of the electrical circuit 18 is, or includes, producing a sound using the sound producing unit 50 when the electrical circuit 18 is enabled. In some embodiments, the sound producing unit 50 can be configured to generate or produce a sound similar to that produced by a conventional medication canister when it is actuated to dispense medication. In this way, the training device 2 can provide feedback to the user or other interested party as to the successful actuation of the training device 2. Alternatively, on activation of the electrical circuit 18 the sound producing unit 50 can produce a different audible sound, for example a beep, or play a voice message, indicating the successful actuation of the training device 2. In further embodiments, which can be in addition to or alternative to the embodiments in which an audible sound is produced, the sound producing unit 50 can produce a sound having a frequency in the ultrasonic range (i.e. outside of the normal range of hearing for a human) when the electrical circuit 18 is activated. This embodiment can be useful where a remote electronic device 19 is provided that can receive the ultrasonic sound, and the ultrasonic sound can be used to convey information on the operation or use of the training device 2 to the remote electronic device 19.

In some embodiments, the electrical circuit 18 comprises a light producing unit 52, for example a light bulb or light emitting diode (LED), and the function of the electrical circuit 18 is, or includes, activating the light producing unit 52 when the electrical circuit 18 is enabled to provide visual feedback. The light can be used to indicate a successful actuation of the training device 2 to the user or other interested party.

In some embodiments, the electrical circuit 18 comprises one or more sensors 54 that, on enabling of the electrical circuit 18, are to measure one or more parameters relating to the use of the training device 2. For example, the sensors 54 can measure the movements of the training device 2 and the inhaler 6, the movements of the training device 2 relative to the inhaler 6 (e.g. the pressing of the training device 2 into the housing 4), the orientation of the training device 2, the force exerted on the training device 2 by the user in attempting to actuate the training device 2, the air flow through the inhaler housing 4 (which can be indicative of the user's breathing and/or whether the user is holding their breath after actuation). Suitable sensors 54 include an accelerometer, a gyroscope, a force sensor, a pressure sensor, an air flow sensor, a microphone (which can be used to listen for the sound of the user's breathing), etc. The electrical circuit 18 can comprise a processor 56 and/or storage device 58 for storing the measurements by the sensors 54, including temporal information on the sensor measurements, i.e. the relative timing and sequence of the measurements. In some embodiments, the electrical circuit 18 can further comprise a feedback device 60 for providing feedback to the user or other interested party on the use of the training device 2 based on the measured one or more parameters. This feedback device 60 can comprise a sound producing unit 50 or light producing unit 52, with the feedback as described above, or it can comprise a display screen. In some embodiments, the feedback device 60 can be configured to provide feedback on a sequence of events performed by the user in using the training device 2. For example, the feedback device 60 can provide feedback on whether the user inhaled through the inhaler 6 at the correct time (i.e. when the training device 2 was moved into the actuated, second, position). It will be appreciated that in some embodiments the feedback device 60 can, based on the measured one or more parameters, provide feedback on how the user can improve their technique or usage of the training device 2.

In some (further or alternative) embodiments, the electrical circuit 18 can comprise a transmitter 62 that can be activated when the electrical circuit 18 is activated to transmit information or data (e.g. obtained by the one or more sensors) on the operation or use of the training device 2 to the remote electronic device 19. The transmitter 62 can operate using any suitable communication protocol, for example, Wi-Fi, Bluetooth, ZigBee, etc.

It will be appreciated that in order to be activated to perform the one or more functions, the electrical circuit 18 will also comprise a power source 64, for example a battery. As noted above, in some embodiments the circuit triggering mechanism 20 can enable the electrical circuit 18 to perform the one or more functions by connecting the electrical circuit 18 to the power source 64. In alternative embodiments, the electrical circuit 18 may be powered by power source 64 all of the time, or in response to the detection of movement of the training device 2 (e.g. when the training device 2 is picked up or inserted into the inhaler housing 4.

In some embodiments, in addition to the electrical circuit 18 being enabled to perform the one or more functions by the closing of the switch 34, the electrical circuit 18 can be configured to monitor other parameters of the use of the training device 2 prior to the actuation of the training device 2 in the inhaler housing 4. For example, the electrical circuit 18 can be configured to monitor movements of the training device 2 before the body 8 is pressed into the second position in the inhaler housing 4. In this case the electrical circuit 18 can comprise an accelerometer or other movement sensor for measuring the movements on the training device 2. These movements might include the shaking of the training device 2 that is required before use of an actual medication canister. In another example, the electrical circuit 18 can be configured to monitor air flow through the housing 4, for example relating to the breathing of the user through the housing 4.

In preferred embodiments, all of the components of the training device 2 are contained within the body 8, i.e. the circuit triggering mechanism 20 (with the exception of the stem 16) and the electrical circuit 18 are contained within the body 8.

The training device 2 can be formed from any suitable material. For example, the body 8 can be formed from plastic or metal (similar to a conventional medication canister). An inhaler housing 4 is typically formed from plastic.

Figure 5:
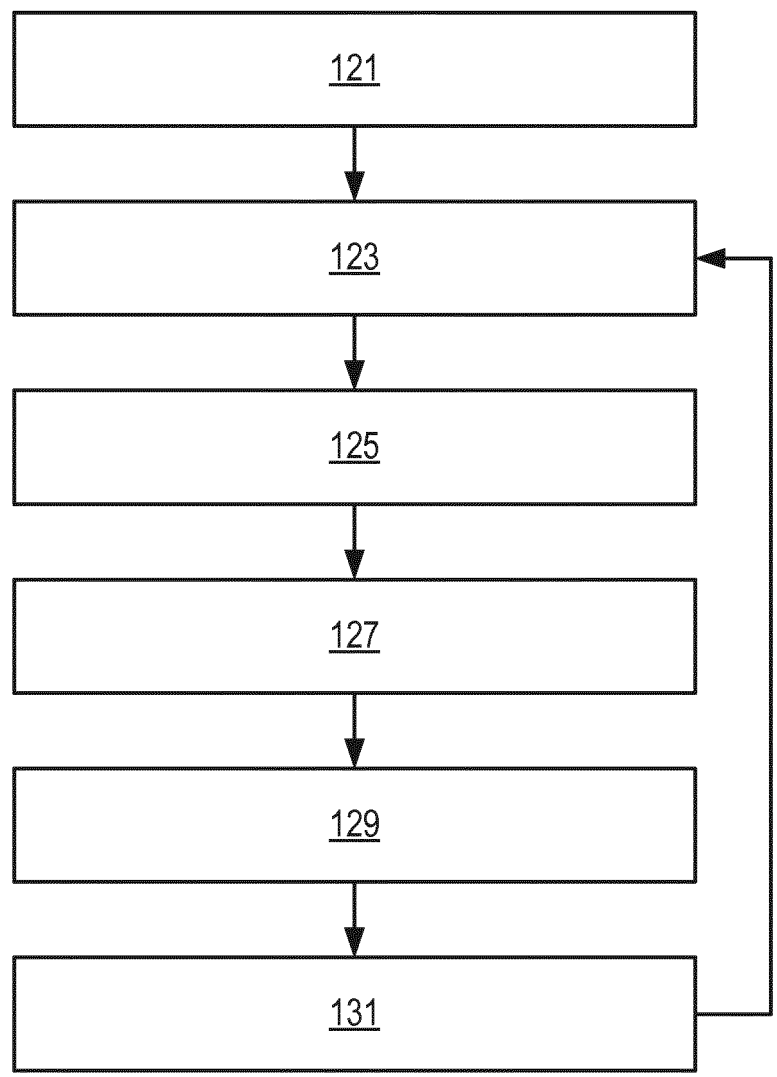
FIG. 5 is a flow chart illustrating a method of using a training device according to an embodiment.

An exemplary method of using a training device 2 according to an embodiment is shown in FIG. 5. In a first step, step 121, a training device 2 as described above is inserted into or connected to an inhaler housing 4. That is, an interface 10 on the training device 2 is used to connect the training device 2 to a canister interface 12 in the housing 4. Step 121 can be performed when a user or patient is to be trained on the use of an inhaler 6, or their technique is to be evaluated. Prior to step 121, the method may comprise removing a conventional medication canister from the inhaler housing 4.

Next, in step 123, a user presses the body 8 of the training device 2 into the inhaler 6, and in particular in the direction shown by arrow 22 in FIG. 2. With a circuit triggering mechanism 20 as shown in FIG. 3, this pressing and movement of the body 8 into the inhaler 6 compresses the resilient component 35 until the switch 34 is closed, thereby enabling the electrical circuit 18 (step 125).

On enabling of the electrical circuit 18, the one or more sensors 54 in the electrical circuit 18 measure one or more parameters relating to the use of the training device 2 (step 127).

The user then releases the pressure on the body 8 and the resilient component 35 acts to return the body 8 to its initial position with respect to the inhaler housing 4 (step 129). This movement disengages or opens the switch 34. In some embodiments, this opening of the switch can disable the electrical circuit 18 or otherwise prevent the electrical circuit 18 from performing the one or more functions. In alternative embodiments, the electrical circuit 18 can remain enabled even after the switch 34 is opened, for example to enable the one or more sensors 54 to continue monitoring the use of the inhaler 6.

Finally, in step 131, the measurements by the one or more sensors 54 are used to provide feedback to the user or other interested party on the use of the inhaler 6.

The method then returns to step 123 for the next training event or session.

There is therefore provided an improved training device for an inhaler, such as a pMDI, that allows a patient to safely practice their inhaler technique to optimise delivery of medication when using an actual medication inhaler.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other processing unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A training device for use in an inhaler in place of a medication canister, the training device comprising:
   a canister-shaped body that is configured to be received at a first position in a housing of an inhaler, wherein the body comprises an interface arranged to connect to a canister interface in the housing of the inhaler;
   an electrical circuit configured to perform one or more functions; and
   a circuit triggering mechanism that comprises a switch for enabling the electrical circuit to perform the one or more functions when the switch is closed, wherein the circuit triggering mechanism is configured such that the switch is closed when the body is pressed from the first position towards the canister interface and into a second position in the housing of the inhaler; wherein the electrical circuit and circuit triggering mechanism are contained within the body.

2. A training device as claimed in claim 1, wherein the circuit triggering mechanism comprises a resilient component configured to provide a force that resists the pressing of the body into the housing of the inhaler.

3. A training device as claimed in claim 2, wherein the resilient component is configured to return the body to the first position in the inhaler when the body is not pressed.

4. A training device as claimed in claim 2, wherein the resilient component comprises a spring or a spring-like component.

5. A training device as claimed in claim 2, wherein the resilient component is disposed within the canister-shaped body.

6. A training device as claimed in claim 1, wherein the distance between the first position and the second position corresponds to the distance moved by a medication canister received in the housing of the inhaler when medication is to be dispensed.

7. A training device as claimed in claim 1, wherein the electrical circuit comprises a sound producing unit, and wherein the one or more functions comprises the sound producing unit producing a sound.

8. A training device as claimed in claim 7, wherein the sound produced comprises auditory feedback for the user.

9. A training device as claimed in claim 8, wherein the sound comprises ultrasonic sound.

10. A training device as claimed in claim 1, wherein the electrical circuit comprises a light producing unit, and wherein the one or more functions comprises the light producing unit producing light.

11. A training device as claimed in claim 1, wherein the electrical circuit comprises one or more sensors, and wherein the one or more functions comprises operating the sensors to measure one or more parameters relating to use of the training device by a user.

12. A training device as claimed in claim 11, wherein the one or more parameters comprises any one or more of movements of the training device, movements of the training device relative to the housing of the inhaler, orientation of the training device, a force exerted on the training device, the air flow through the housing of the inhaler and whether a user is holding their breath after the body is moved to the second position.

13. A training device as claimed in claim 11, wherein the electrical circuit further comprises a feedback device for providing feedback to the user on the use of the training device based on the measured one or more parameters.

14. A training device as claimed in claim 11, wherein the electrical circuit further comprises a transmitter for transmitting the measurements of the one or more parameters to a remote electronic device.

15. A training device as claimed in claim 1, wherein the electrical circuit is further configured to monitor movements of the training device before the body is pressed into the second position in the housing of the inhaler.

16. A training device as claimed in claim 1, wherein the electrical circuit is further configured to monitor air flow through the housing of the inhaler before the body is pressed into the second position in the housing of the inhaler.

17. A training device as claimed in claim 1, wherein the triggering mechanism comprises a stem disposed proximate to the interface.

18. A training device as claimed in claim 17, wherein the stem is coupled to a resilient member and the switch, each disposed within the cannister-shaped body.

19. An inhaler, comprising:
a housing having a canister interface; and
a training device as claimed in claim 1.

20. A method of training a user to operate an inhaler, the method comprising:
providing a training device that is for use in the inhaler in place of a medication canister and that comprises a canister-shaped body that is configured to be received at a first position in a housing of the inhaler, wherein the body comprises an interface arranged to connect to a canister interface in the housing of the inhaler, an electrical circuit configured to perform one or more functions, and a circuit triggering mechanism that comprises a switch for enabling the electrical circuit to perform the one or more functions when the switch is closed, and wherein the circuit triggering mechanism is configured such that the switch is closed when the body is pressed from the first position towards the canister interface and into a second position in the housing of the inhaler, wherein the electrical circuit and circuit triggering mechanism are contained within the body; and
enabling the electrical circuit to perform the one or more functions when the body is pressed into the second position in the inhaler.

\* \* \* \* \*